United States Patent [19]

Kamioka et al.

[11] Patent Number: 5,191,869

[45] Date of Patent: Mar. 9, 1993

[54] GASOLINE NATURE SENSING SYSTEM

[75] Inventors: Hideki Kamioka; Masahiko Shimamura, both of Gumma, Japan

[73] Assignee: Japan Electronic Control Systems Co., Ltd., Isezaki, Japan

[21] Appl. No.: 853,660

[22] Filed: Mar. 19, 1992

[30] Foreign Application Priority Data

Oct. 9, 1991 [JP] Japan .................................. 3-290942

[51] Int. Cl.⁵ ........................................... F02M 51/00
[52] U.S. Cl. .................................... 123/494; 123/1 A
[58] Field of Search ............... 123/494, 1 A, 362, 381, 123/575; 73/61.1 R, 117.3

[56] References Cited

U.S. PATENT DOCUMENTS

| 4,905,655 | 3/1990 | MacKawa | 123/494 |
| 4,971,615 | 11/1990 | Gonze | 123/444 |
| 4,982,709 | 1/1991 | Oota | 123/1 A |
| 4,989,570 | 2/1991 | Kuribara et al. | 123/494 |
| 5,005,402 | 4/1991 | Pischinger et al. | 123/1 A |
| 5,060,619 | 10/1991 | Sakurai et al. | 123/1 A |
| 5,086,745 | 2/1992 | Nuhimura et al. | 123/494 |

FOREIGN PATENT DOCUMENTS 4-8956 1/1982 Japan .................................. 123/494

Primary Examiner—Raymond A. Nelli
Attorney, Agent, or Firm—Foley & Lardner

[57] ABSTRACT

A system for sensing the nature of gasoline is disclosed, which comprises a capacitance type sensor for producing a first information signal representative of the dielectric constant of the gasoline; a temperature sensor for producing a second information signal representative of the temperature of the gasoline; a temperature coefficient deriving device for deriving a temperature coefficient of the gasoline from the first and second information signals; an additive concentration deriving device for deriving the concentration of alcohols in the gasoline from the temperature coefficient; a correcting device for correcting the first information signal in view of a reference temperature; and a judging device for judging the nature of the gasoline from the derived concentration of the additive and the corrected first information signal.

7 Claims, 6 Drawing Sheets

GASOLINE NATURE SENSING SYSTEM

BACKGROUND OF THE INVENTION

1. Field of the Invention

The present invention relates in general to fuel nature sensors used in a motor vehicle, and more particularly, to fuel nature sensors of a type which can sense the nature of gasoline used as fuel for internal combustion engines of the vehicle. More specifically, the present invention is concerned with a gasoline nature sensing system which can determine whether the gasoline fed to the engine is light gasoline, medium gasoline or heavy gasoline.

2. Description of the Prior Art

Gasoline used as fuel for automotive engines is generally grouped into three, which are light gasoline which contains as major components chain hydrocarbons such as heptane, pentane or the like, heavy gasoline which contains as major components aromatic hydrocarbons such as benzene or the like and medium gasoline which lies between the light gasoline and the heavy gasoline. Due to the nature of the major components contained therein, the light gasoline is easy to evaporate, while the heavy gasoline is hard to evaporate.

Usually, automotive engines are set to use the light gasoline. However, nowadays, for dealing with the energy shortage and the air pollution suppression law, it has been proposed to use as the fuel of the automotive engines the heavy gasoline.

However, if the heavy gasoline is used in an engine which has been set to use the light gasoline, undesired ignition delay tends to occur causing a lean combustion in the engine. This lean combustion brings about not only poor startability of the engine but also poor operability of the same. Furthermore, usage of such heavy gasoline in such engine tends to induce undesired discontinuous combustion in the engine under cruising of the vehicle. The discontinuous combustion causes increase in harmful components in exhaust gas from the engine.

While, if the light gasoline is used in an engine which has been set to use the heavy gasoline, over-rich combustion tends to occur in the engine, which brings about a so-called "smoking" near the ignition plugs.

In order to solve the above-mentioned drawbacks, a system has been proposed by the same applicants, which is disclosed in Japanese Utility Model First Provisional Publication 4-8956. The system embodies the theory that the dielectric constant of gasoline has a closed relationship with the nature of the same. That is, the dielectric constant of heavy gasoline is greater than that of light gasoline.

In the system, a capacitance detector is used for producing an information on the dielectric constant. The capacitance detector comprises spaced electrode plates which are submerged in gasoline. Electric capacitance established between the spaced electrode plates is treated by an oscillating means which generates pulses whose frequency is based on the capacitance. A frequency-voltage converting means converts the frequency to a corresponding voltage. A judging means judges whether the gasoline is the light gasoline or the heavy gasoline by comparing the converted voltage with a reference voltage.

However, some gasoline put on the market nowadays is of a type which contains as additive agents alcohols such as methanol, ethanol, methyltertialbutylether (MTBE) and the like. Due to addition of such agents, the dielectric constant of the gasoline is increased as is understood from the graph of FIG. 9.

Due to its inherent construction, the above-mentioned conventional system can not deal with such gasoline. That is, as is seen from the graph of FIG. 9, the output voltage "V0" from the frequency-voltage converting means may appear in three cases, one being for heavy gasoline without alcohols, one being for medium gasoline with 5% of alcohols and the other being for light gasoline with 10% of alcohols. This means that the above-mentioned conventional system can not detect the nature of the gasoline any longer.

SUMMARY OF THE INVENTION

It is therefore an object of the present invention to provide a gasoline nature sensing system which is free of the above-mentioned drawbacks.

According to the present invention, there is provided a gasoline nature sensing system which can accurately sense the nature (viz., light, medium or heavy) of gasoline even when the gasoline contains additive agents.

According to a first aspect of the present invention, there is provided a system for sensing the nature of gasoline. The system comprises a capacitance type sensor for producing a first information signal representative of the dielectric constant of the gasoline; a temperature sensor for producing a second information signal representative of the temperature of the gasoline; temperature coefficient deriving means for deriving a temperature coefficient of the gasoline from the first and second information signals; additive concentration deriving means for deriving the concentration of any additive in the gasoline from the temperature coefficient; correcting means for correcting the first information signal in view of a reference temperature; and judging means for judging the nature of the gasoline from the derived concentration of the additive and the corrected first information signal.

According to a second aspect of the present invention, there is provided a system which comprises a fuel injection type internal combustion engine including spark plugs and fuel injectors; a fuel tank; a fuel pipe extending from the fuel tank to the fuel injectors; a capacitance type sensor connected to the fuel pipe for producing a first information signal representative of the dielectric constant of the gasoline; a temperature sensor connected to the fuel pipe for producing a second information signal representative of the temperature of the gasoline; temperature coefficient deriving means for deriving a temperature coefficient of the gasoline from the first and second information signals; additive concentration deriving means for deriving the concentration of any additive in the gasoline from the temperature coefficient; correcting means for correcting said first information signal in view of a given temperature; judging means for judging the nature of the gasoline from the derived concentration of the additive and the corrected first information signal; and means for controlling the spark plugs and the fuel injectors in accordance with the judgement made by the judging means.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

In the following, the present invention will be described in detail with reference to FIGS. 1 to 8 of the accompanying drawings.

Figure 1:
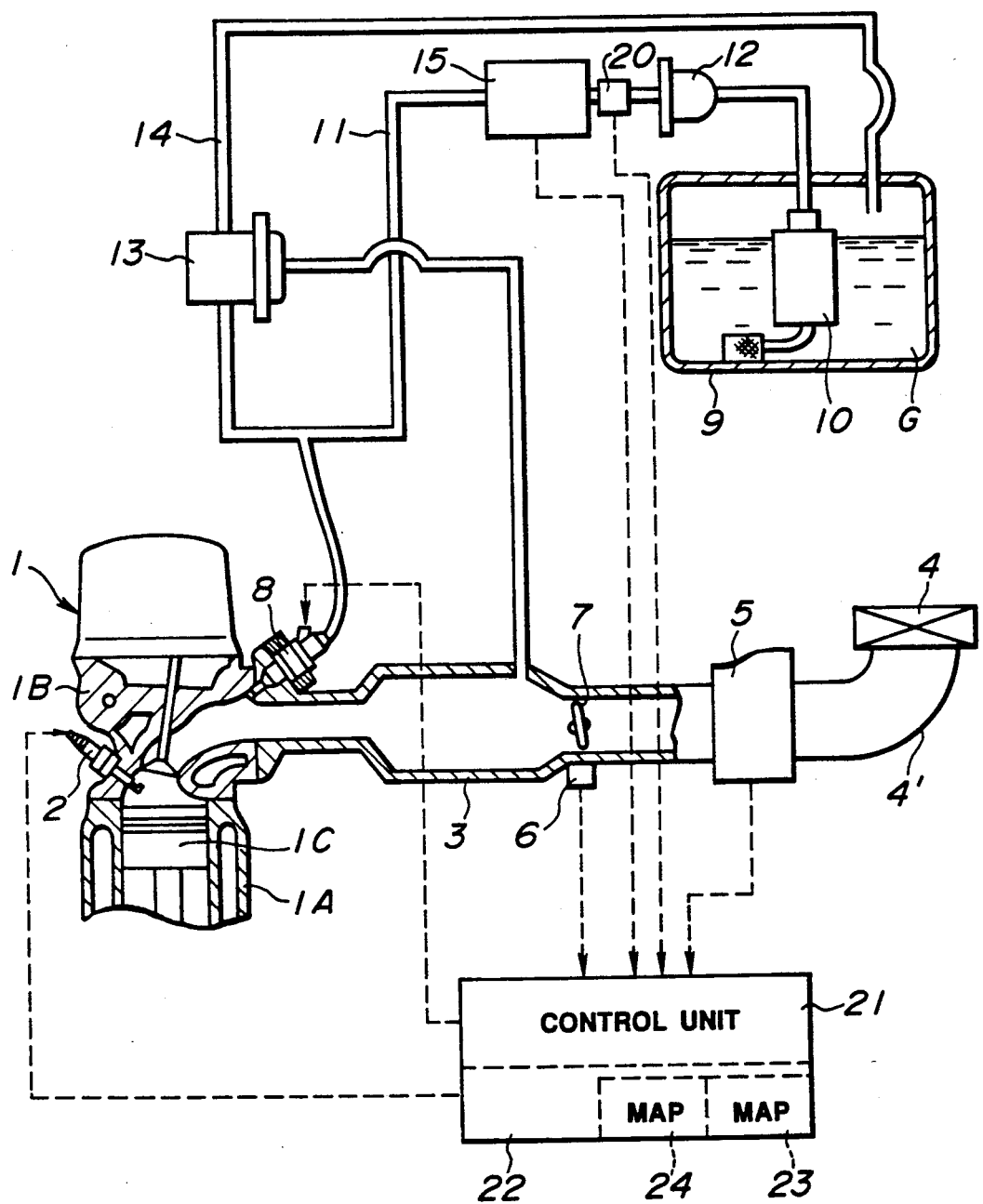
FIG. 1 is a schematic view of an electronically controlled fuel injection type internal combustion engine to which the present invention is practically applied.

In FIG. 1, there is shown an electronically controlled fuel injection type internal combustion engine to which the present invention is practically applied.

Designated by numeral 1 is a four cylinder type internal combustion engine which comprises generally a cylindrical block 1A, a cylindrical head 1B mounted on the cylinder block 1A, and four pistons 1C reciprocatively movably received in cylinder bores of the cylinder block 1A. Designated by numeral 2 are ignition plugs which are mounted to the cylinder head 1B having their plug heads exposed to respective combustion chambers of the cylinder bores. Each ignition plug 2 ignites the combustible mixture in the corresponding combustion chamber when an aftermentioned control unit 21 issues an ignition instruction signal.

Designated by numeral 3 is an intake manifold whose branched base portion is secured to an intake side of the cylinder head 1B. The intake manifold 3 has an upstream end from which an intake tube 4' extends. The intake tube 4' has an upstream end on which an air filter 4 is mounted. An air-flow meter 5 is arranged in the intake tube 4' to measure air quantity passing therethrough. Designated by numeral 7 is a throttle valve which is arranged downstream of the air-flow meter 5. Designated by numeral 6 is a throttle valve switch 6 which issues an information signal representative of the inclination angle of the throttle valve 7. Designated by numeral 8 are fuel injectors each being arranged to inject fuel into the corresponding combustion chamber upon receiving a fuel injection instruction signal from the control unit 21.

Designated by numeral 9 is a fuel tank in which gasoline G is contained. Within the fuel tank 9, there is installed an in-tank type fuel pump 10. Designated by numeral 11 is a fuel pipe which has an upstream end connected through a fuel filter 12 to an outlet port of the fuel pump 10. The fuel pipe 11 has two downstream ends, one being connected to the fuel injectors 8 and the other being connected to an inlet port of a pressure regulator 13. Designated by numeral 14 is a fuel return pipe which extends from an outlet port of the pressure regulator 13 to the fuel tank 9.

Designated by numeral 15 is a capacitance type sensor which is connected to the fuel pipe 11 at a position downstream of the fuel filter 12.

As will become apparent from the following, the capacitance type sensor 15 is constructed to issue a voltage signal which represents the dielectric constant or the nature of gasoline flowing in the fuel pipe 11.

Figure 2:
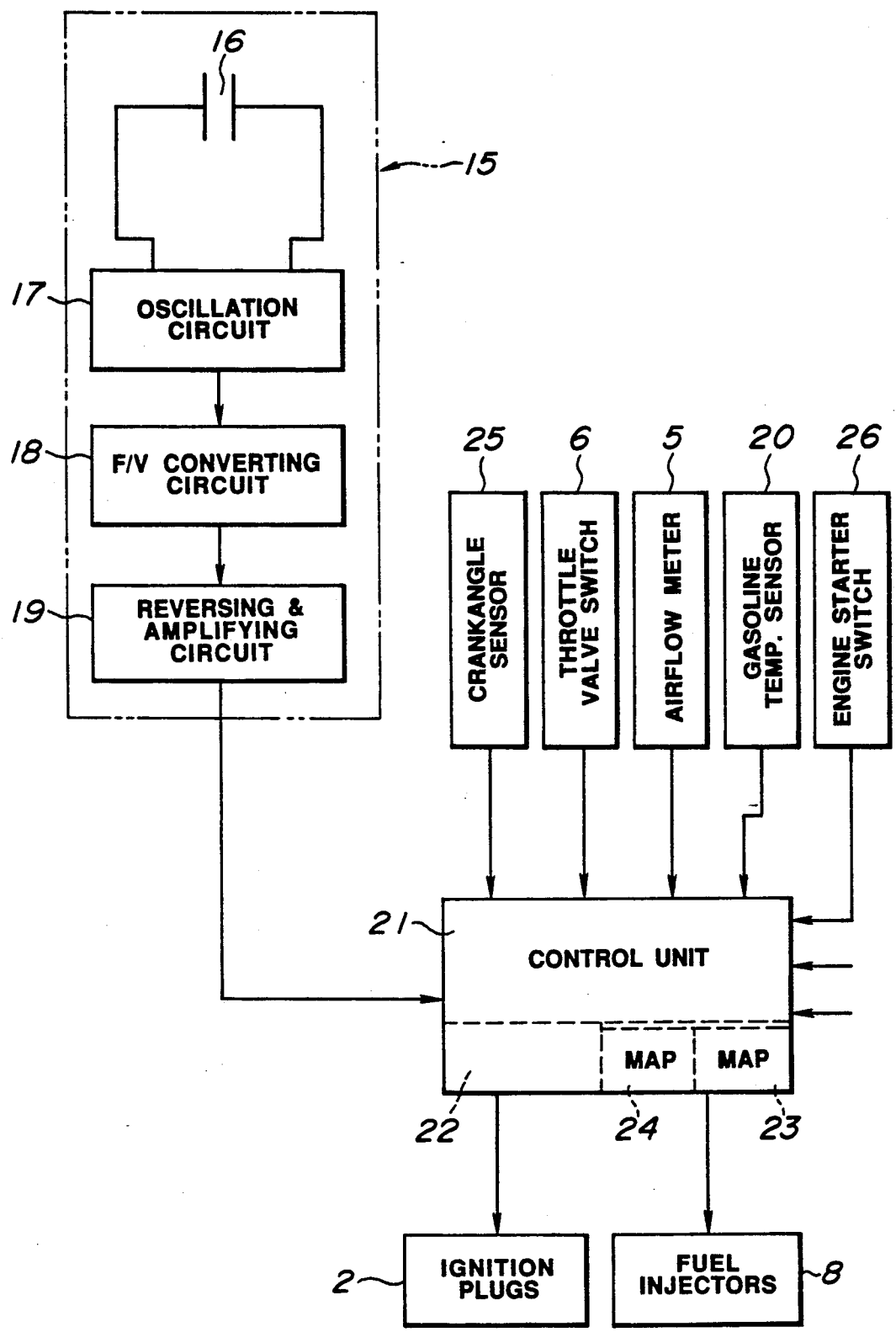
FIG. 2 is a block diagram of a control system of the internal combustion engine.

As is seen from FIG. 2, the capacitance type sensor 15 comprises two parallel electrode plates 16 which are located in the fuel pipe 11. When the electrode plates are submerged in gasoline, there is established a capacitance "C" between the electrode plates, which is represented by the following equation:

$$C = \epsilon_1 \times S_1 / d_1 \quad (1)$$

wherein:
$\epsilon_1$ ... dielectric constant of gasoline;
$S_1$ ... surface area of each electrode plate;
$d_1$ ... distance between electrode plates.

A LC type oscillation circuit 17 is used for generating pulses whose frequency "f" is based on the capacitance "C". The frequency "f" is represented by the following equation:

$$f = \tfrac{1}{2}\pi L \sqrt{C + C_0} \quad (2)$$

wherein:
L ... inductance; 'C0 ... capacitance of circuit.

A frequency-voltage converting circuit 18 is used for converting the frequency "f" to a voltage "E", and a reversing-amplification circuit 19 is further used for producing an output voltage "V" by reversing and amplifying the voltage "E" from the frequency-voltage converting circuit 19.

The following table I shows major components of two types (light and heavy) of gasoline and the dielectric constants thereof.

TABLE 1

| Hydrocarbons | Dielectric Constant | Type |
| --- | --- | --- |
| pentane | 1.892 | light gasoline |
| heptane | 1.924 | light gasoline |
| benzene | 2.284 | heavy gasoline |

Figure 3:
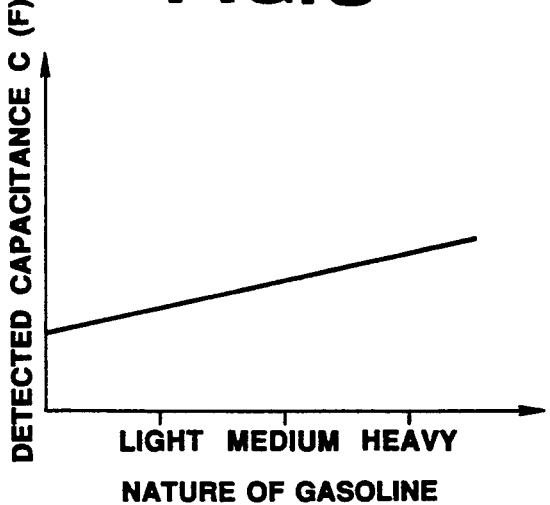
FIG. 3 is a graph showing the relationship between the nature of gasoline and the capacitance detected by a capacitance detector.

The electric capacitance "C" established between the two electrode plates 16 submerged in such pure gasoline shows such a characteristic as shown in the graph of FIG. 3. It is to be noted that the pure gasoline is gasoline which has no alcohols contained therein.

Figure 4:
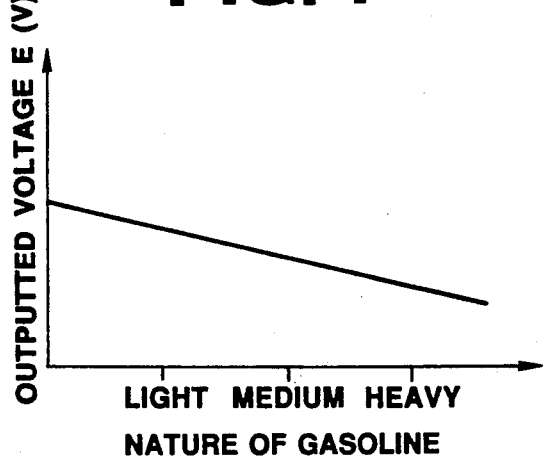
FIG. 4 is a graph showing the relationship between the nature of gasoline and the voltage outputted from a frequency-voltage converting circuit.
Figure 5:
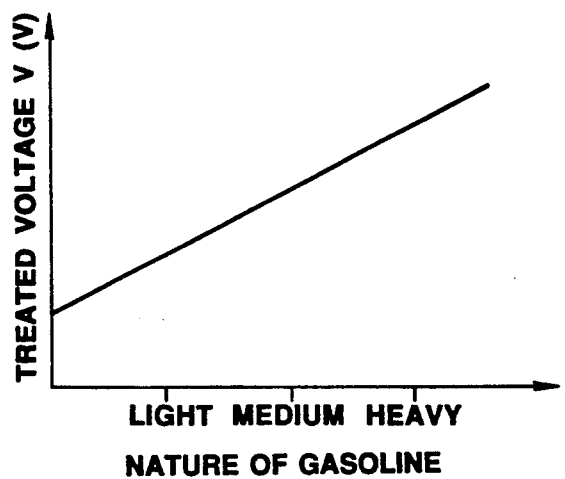
FIG. 5 is a graph showing the relationship between the nature of gasoline and the voltage outputted from a reversing-amplification circuit.

The voltage "E" outputted from the frequency-voltage converting circuit 18 shows such a characteristic as shown in the graph of FIG. 4, and the voltage "V" outputted from the reversed-amplification circuit 19 shows such a characteristic as shown in the graph of FIG. 5.

That is, from the capacitance type sensor 15, there is outputted a voltage signal having such a characteristic as shown in the graph of FIG. 5.

Referring back to FIG. 1, designated by numeral 20 is a gasoline temperature sensor which is connected to the fuel pipe 11 to detect the temperature of gasoline flowing therethrough. That is, the gasoline temperature sensor 20 feeds the control unit 21 with an information signal representing the temperature of the gasoline "G".

If desired, the gasoline temperature sensor 20 and the above-mentioned capacitance type sensor 15 may be installed in the fuel tank 9.

The control unit 21 is constructed of a microcomputer which comprises a CPU, a memory circuit 22 consisting of RAM and ROM and input and output interfaces. The memory circuit 22 memorizes various control programs which are a program for judging the nature of gasoline flowing in the fuel pipe 11, a program for calculating the amount of fuel injected by the fuel injectors 8, a program for calculating the ignition timing of the ignition plugs 2 and the like. The memory circuit 22 further memorizes a characteristic map 23 of FIG. 6 and a nature judging map 24 of FIG. 7.

Figure 6:
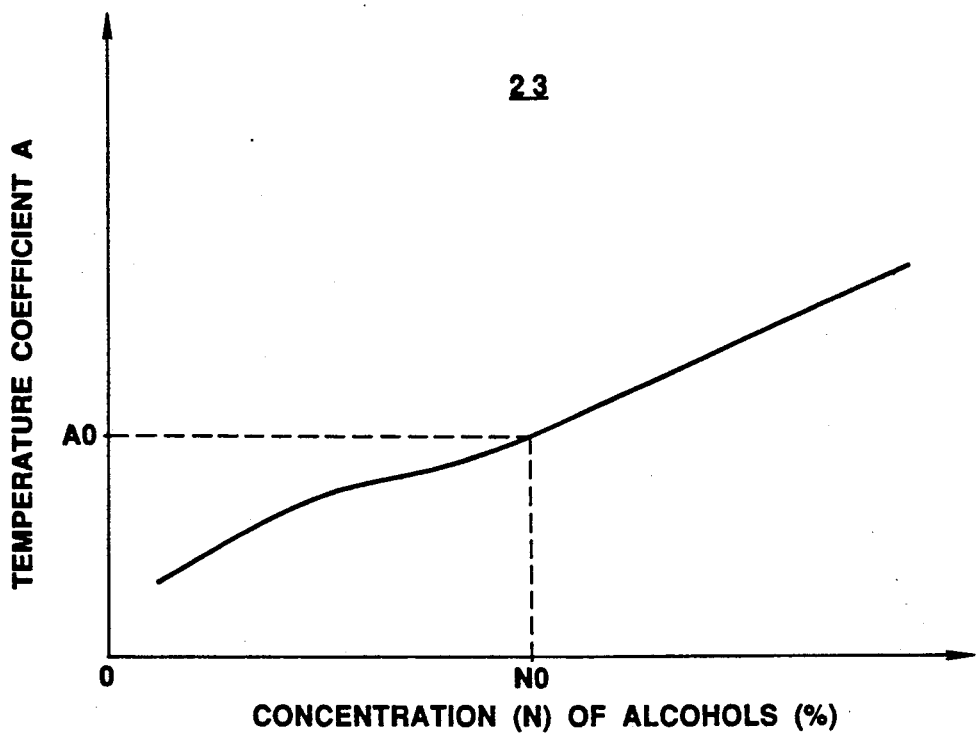
FIG. 6 is a characteristic map memorized in a memory circuit of a control unit, which shows the relationship between the concentration of alcohols in gasoline and the temperature coefficient.

The characteristic map of FIG. 6 is used for feeding the CPU with an information on the relationship between the concentration of additive agents in gasoline and the temperature coefficient.

Figure 7:
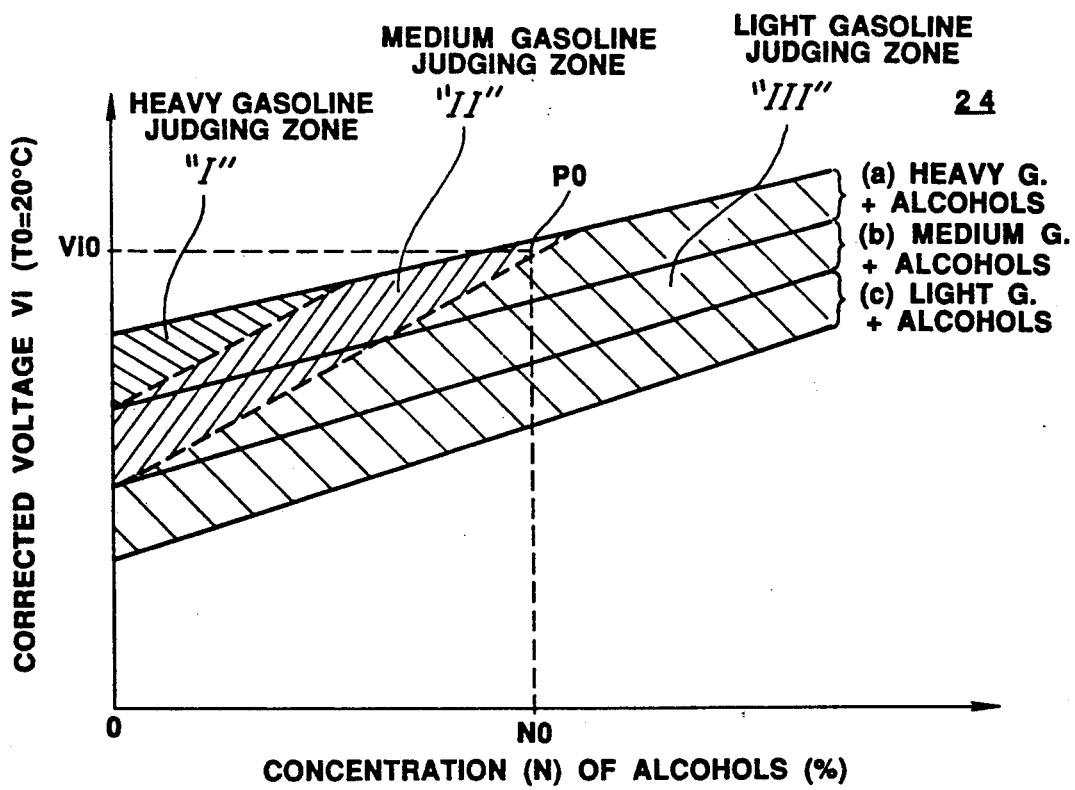
FIG. 7 is a nature judging map memorized in the memory circuit of the control unit.

The nature judging map 24 of FIG. 7 is also used as an information material fed to the CPU. The map is illustrated on a X-Y coordinate which has on the axis of abscissas the concentration (%) of alcohols in gasoline and on the axis of ordinates a voltage "Vi" which is corrected in view of a reference temperature (T0=20° C.) of gasoline.

It is to be noted that in the map of FIG. 7 three parallel zones (a), (b) and (c) are shown, which are respectively provided by heavy, medium and light gasolines with alcohols contained therein. Because alcohols used as additive agents of gasolines have a tendency of increasing the dielectric constant of the gasolines, addition of the alcohols to the gasolines induces softening of the gasolines.

It is further to be noted that the finely hatched zone "I" is used for determining the heavy gasoline, the other finely latched zone "II" is for determining the medium gasoline and the coarsely hatched zone "III" is for determining the light gasoline. That is, the line "I–" is the boundary line provided when the heavy gasoline changes its nature to that of medium gasoline and to that of light gasoline due to addition of alcohols thereinto and the line "II-III" is the boundary line provided when the medium gasoline changes its nature to that of light gasoline due to addition of alcohols thereinto.

As is seen from FIG. 2, information signals from the air-flow meter 5, the throttle valve switch 6, a crankangle sensor 25, the capacitance type sensor 15, the gasoline temperature sensor 20 and an engine starter switch 26 are fed to the control unit 21, and instruction signals produced by the control unit 21 are fed to the ignition plugs 2 and the fuel injectors 8. Although not shown in the drawing, information signals from an engine cooling water temperature sensor and an air/fuel ratio sensor are also fed to the control unit 21.

Figure 8:
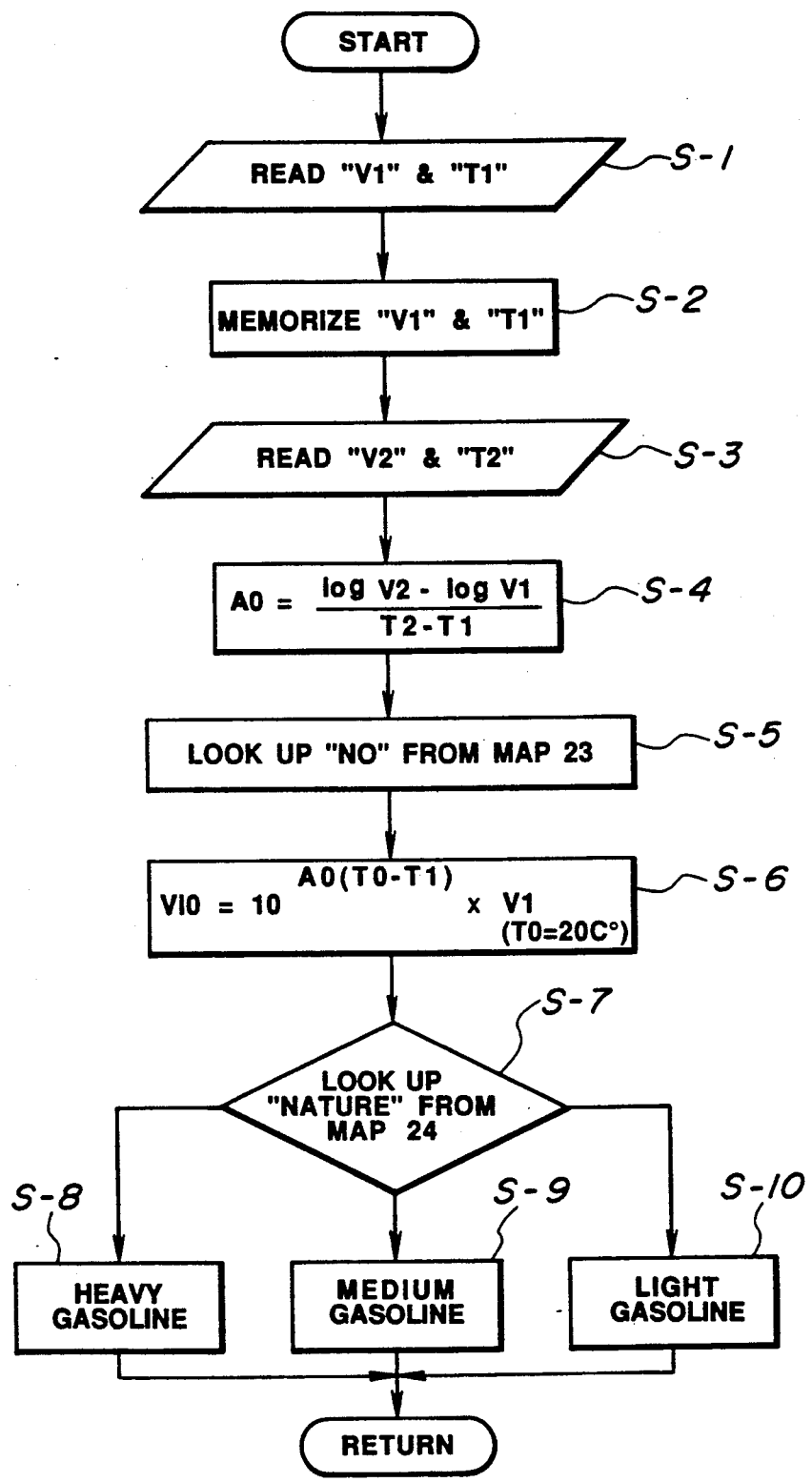
FIG. 8 is a flowchart showing operation steps programmed in the control unit.
Figure 9:
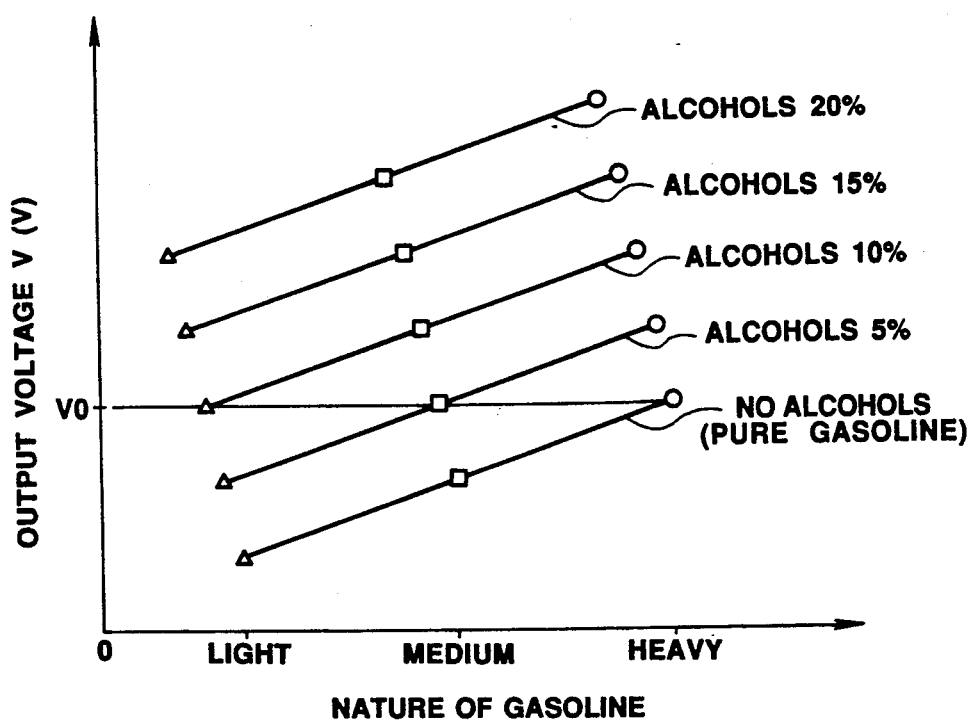
FIG. 9 is a graph showing the relationship between the nature of gasoline and the voltage outputted from a frequency-voltage converting circuit, with respect to the concentration of alcohols in the gasoline.

In the following, the operation steps for judging the nature of gasoline will be described with reference to the flowchart of FIG. 8.

When the engine starter switch 26 is turned ON, the operation flow goes to step 1. At this step, the output voltage V1 from the capacitance type sensor 15 and the temperature information T1 from the gasoline temperature sensor 20 are read. These data are memorized (step 2) for a given time. After the given time, the operation flow goes to step 3. At this step, the output voltage V2 from the capacitance type sensor 15 and the temperature information T2 from the gasoline temperature sensor 20 are read again. Then, at step 4, the temperature coefficient "A0" is calculated by using the following equation:

$$A0 = (\log V2 - \log V1)/(T2 - T1) \tag{3}$$

Then, the operation flow goes to step 5. At this step, the concentration "N0" of alcohols is derived from the calculated temperature coefficient "A0" with reference to the characteristic map 23 (see FIG. 6).

Then, at step 6, a corrected voltage "Vi0" at the reference temperature (20° C.) is calculated from the following equation:

$$Vi0 = 10^{A0(T0-T1)} \times V1 \tag{4}$$

Then, the operation flow goes to step 7. At this step, the nature judging map 24 (see FIG. 7) is used for judging the nature of the gasoline. That is, a point "P0" satisfying both the concentrations "N0" given at step 5 and the corrected voltage "Vi0" given at step 6 is plotted on the nature judging map 24.

If, for example, the point "P0" is located in the medium gasoline judging zone "II" as is shown in the map 24 of FIG. 7, it is judged that the gasoline is of the medium type (step 9). In this case, corresponding instruction signals suitable for achieving the optimum engine operation on medium gasoline are fed from the control unit 21 to the ignition plugs 2 and the fuel injectors 8. While, if the point "P0" is located in the heavy gasoline judging zone "III", it is judged that the gasoline is of the heavy type (step 8), and if the point "P0" is located in the light gasoline judging zone "III", it is judged that the gasoline is of the light type (step 10).

As will be understood from the foregoing description, the judgement as to whether gasoline is of heavy, medium or light type is carried out by skillfully computing the output voltage from the capacitance type sensor 15 and the temperature information from the gasoline temperature sensor 20. Furthermore, in the invention, the judgement is carried out in such a manner as to remove the influence of the alcohols contained in the gasoline, and thus a highly reliable judgement of the gasoline nature is available in the present invention.

What is claimed is:

1. A system for sensing the nature of gasoline, comprising:

a capacitance type sensor for producing a first information signal representative of the dielectric constant of the gasoline;

a temperature sensor for producing a second information signal representative of the temperature of the gasoline;

temperature coefficient deriving means for deriving a temperature coefficient of the gasoline from said first and second information signals;

additive concentration deriving means for deriving the concentration of any additive in the gasoline from said temperature coefficient;

correcting means for correcting said first information signal in view of a reference temperature; and judging means for judging the nature of the gasoline from the derived concentration of the additive and the corrected first information signal.

2. A system as claimed in claim 1, in which said temperature coefficient deriving means derives the temperature coefficient "A0" of the gasoline by using the following equation:

$$A0 = (\log V2 - \log V1)/(T2 - T1)$$

wherein:
- V1 ... output voltage from the capacitance type sensor at a first given time;
- V2 ... output voltage from the capacitance type sensor at a second given time;
- T1 ... temperature of the gasoline at the first given time; and
- T2 ... temperature of the gasoline at the second given time.

3. A system as claimed in claim 2, in which said correcting means produces the corrected first information signal "Vi0" by using the following equation:

$$Vi0 = 10^{A0(T0-T1)} \times V1$$

wherein:
- T0 ... reference temperature.

4. A system as claimed in claim 3, in which said judging means judges whether the gasoline is of heavy, medium or light type.

5. A system as claimed in claim 1, in which said any additive is alcohol contained in the gasoline.

6. A system as claimed in claim 5, in which said capacitance type sensor comprises spaced electrode plates which are submerged in the gasoline to establish therebetween an electric capacitance which varies in accordance with the dielectric constant of the gasoline.

7. A system comprising:
- a fuel injection type internal combustion engine including spark plugs and fuel injectors;
- a fuel tank;
- a fuel pipe extending from said fuel tank to said fuel injectors;
- a capacitance type sensor connected to said fuel pipe for producing a first information signal representative of the dielectric constant of the gasoline;
- a temperature sensor connected to said fuel pipe for producing a second information signal representative of the temperature of the gasoline;
- temperature coefficient deriving means for deriving a temperature coefficient of the gasoline from said first and second information signals;
- additive concentration deriving means for deriving the concentration of any additive in the gasoline from said temperature coefficient;
- correcting means for correcting said first information signal in view of a given temperature;
- judging means for judging the nature of the gasoline from the derived concentration of the additive and the corrected first information signal; and
- means for controlling said spark plugs and said fuel injectors in accordance with the judgement made by said judging means.

* * * * *